United States Patent [19]

Hoke

[11] 4,208,357
[45] Jun. 17, 1980

[54] PROCESS FOR PREPARING PHOSPHORUS AND SULFUR CONTAINING AMIDES AND THIOAMIDES

[75] Inventor: Donald I. Hoke, Chagrin Falls, Ohio

[73] Assignee: The Lubrizol Corporation, Wickliffe, Ohio

[21] Appl. No.: 942,096

[22] Filed: Sep. 13, 1978

Related U.S. Application Data

[60] Division of Ser. No. 759,614, Jan. 17, 1977, which is a continuation-in-part of Ser. No. 503,892, Sep. 6, 1974, Pat. No. 4,032,461.

[51] Int. Cl.² .................. C07F 9/165; C07F 9/38; C07F 9/30
[52] U.S. Cl. ......................... 260/978; 260/978
[58] Field of Search ........................ 260/978

[56] References Cited

U.S. PATENT DOCUMENTS

| 2,566,129 | 8/1951 | Hook et al. | 260/978 |
| 2,566,288 | 8/1951 | Hook et al. | 260/978 |
| 2,586,656 | 2/1952 | Hook et al. | 260/978 |
| 2,630,451 | 3/1953 | Fletcher et al. | 260/978 |
| 2,709,156 | 5/1955 | Bishop et al. | 260/978 |
| 2,736,707 | 2/1956 | Morris | 252/46.7 |
| 3,517,088 | 6/1970 | Gutman et al. | 260/928 |

*Primary Examiner*—Anton H. Sutto
*Attorney, Agent, or Firm*—Daniel N. Hall; William H. Pittman; Raymond F. Keller

[57] ABSTRACT

Compounds having the formula:

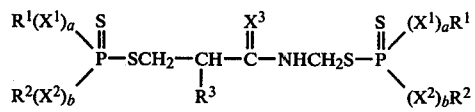

wherein each $R^1$ and $R^2$ is a hydrocarbon-based radical; $R^3$ is a member selected from the group consisting of hydrogen, halogen, lower alkyl, and substituted lower alkyl; each of $X^1$, $X^2$ and $X^3$ is oxygen or sulfur; and a and b are each 0 or 1, are useful as lubricant additives and have insecticidal and pesticidal properties.

9 Claims, No Drawings

PROCESS FOR PREPARING PHOSPHORUS AND SULFUR CONTAINING AMIDES AND THIOAMIDES

This application is a division of my co-pending application Ser. No. 759,614 filed Jan. 17, 1977 which was a continuation-in-part of my then co-pending application Ser. No. 503,892, filed Sept. 6, 1974, now U.S. Pat. No. 4,032,461.

This invention relates to novel amides and thioamides containing phosphinothioylthio substituents, to a method for their preparation, and to lubricating compositions containing said amides and thioamides as additives therein.

The compounds of this invention have the formula

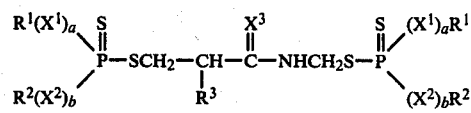

wherein each of $R^1$ and $R^2$ is a substantially saturated hydrocarbon-based radical; $R^3$ is hydrogen, halogen, lower alkyl or substituted lower alkyl; each of $X^1$, $X^2$ and $X^3$ is oxygen or sulfur; and a and b are each 0 or 1. These compounds have the properties of being oxidation inhibitors, corrosion inhibitors, anti-wear agents, and extreme pressure agents and, accordingly, are useful as additives for lubricating oils to improve these properties in formulated lubricating compositions. They are also useful for their insecticidal and pesticidal properties.

The compounds of this invention are prepared by the reaction of a N-hydroxymethylacrylamide or thioacrylamide having the formula $CH_2=C(R^3)C(X^3)NHCH_2OH$ with an appropriate amount of a suitably substituted phosphinothioylthio compound having the formula $R^1(X^1)_aR^2(X^2)_bP(S)SH$, to produce the desired disubstituted product.

Both of the reactants of the subject preparative process are well known in the art. For example, the substituted phosphinothioylthio compounds are disclosed and methods given for their preparation in U.S. Pat. Nos. 2,767,164; 3,396,109; 3,403,102 and 3,428,561, and 2,802,856. Likewise, the N-hydroxymethylacrylamides and thioacrylamides are reported in the prior art and methods given for their preparation, such as in U.S. Pat. Nos. 2,593,888; 2,760,977; 2,864,861; 2,864,862; 3,064,050; and 3,087,965. The patents are expressly incorporated herein for their disclosure of how to make the above-described reactants.

More specifically, the preparative process for the compounds of the present invention involves the reaction of N-hydroxymethylacrylamide (in which $X^3$ is oxygen and $R^3$ is hydrogen, which is preferred) or N-hydroxymethylthioacrylamide (in which $X^3$ is sulfur and $R^3$ is hydrogen) with the substituted phosphinothioylthio compound in a molar ratio of about two (2) moles of the phosphinothioylthio reactant per mole of the amide or thioamide reactant. Of course, if desired, mixtures of the various reactants can be used, i.e., one or more of the amide and/or thioamide reactants and/or one or more of the substituted phosphinothioylthio reactants may be used. Accordingly, the use of such mixtures comprising one or more of these reactants is contemplated as being within the scope of the present invention as set forth in the appended claims.

The reaction may be conducted in either the presence or absence of added solvents or diluents as reaction media. One convenient method for effecting the reaction is to use a stoichiometric excess of the amide or thioamide reactant and then utilize this excess as the reaction medium. This method is particularly convenient when hydrolytic degradation of the reactants or products is a problem. When an excess of the amide or thioamide reactant is used, the amount of the excess is not critical. Usually, the excess will range from about a one (1) mole excess over the stoichiometric requirement up to about a ten (10) mole excess.

When the reaction is conducted in the presence of an added reaction medium, i.e., one or more substantially inert, normally liquid, organic diluents or solvents, the total amount of the diluent or solvent used is not critical. Ordinarily this diluent will comprise from about 10% to about 80%, and preferably, about 30% to about 70% by weight of the reaction mixture based upon the total weight of the reactants and reaction media in the reaction mixture. By "substantially inert" is meant a material which does not materially interfere with the reaction nor react in any significant amount under the conditions of the reaction as described and exemplified herein.

Suitable diluents or solvents include aromatic hydrocarbons, aliphatic hydrocarbons, chlorinated hydrocarbons, ethers, and the like, such as benzene, toluene, xylene, heptane, octane, dodecane, cyclohexane, methylcyclohexane, kerosene, mineral oil, chlorobenzene, heptyl chloride, 1,4-dioxane, n-propyl ether, methyl n-amyl ether, and mixtures of two or more of these. Selection of specific suitable reaction media is within the skill of the art.

The reaction may be conducted at a temperature of about 0°-100° C. Although the reaction may be conducted above 100° C., dehydration is more likely to occur and, accordingly, the yield of the desired product will be diminished. It is usually preferred to use reaction temperatures of about 25°-80° C. While the reaction is conveniently conducted at atmospheric pressure, it may be conducted at subatmospheric or superatmospheric pressure if desired.

A related aspect of the invention is the posttreatment of the reaction mixture obtained by the reaction of the N-hydroxymethylacrylamide or the corresponding thioacrylamide and the substituted phosphinothioylthio compound with one or more organic epoxides. This post-treatment is particularly advantageous in reducing the acidity of the reaction mixture and also in improving the oil solubility of the reaction mixture.

Organic epoxides useful in the post-treatment of the reaction mixture can have up to about forty (40) carbon atoms, and are represented by the formula

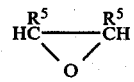

wherein each $R^5$ is individually selected from the group consisting of hydrogen, aliphatic, cycloaliphatic, and aromatic radicals. Normally, each $R^5$ will be hydrogen, alkyl, cycloalkyl or aryl. The lower alkylene and haloalkylene epoxides containing from two (2) to eight (8) carbon atoms are particularly preferred for the posttreatment. Those epoxides in which one of the $R^5$ groups is hydrogen, i.e., terminal epoxides, are particularly preferred. Specific examples of organic epoxides useful for this post-treatment process are ethylene oxide, propylene oxide, 1,2-epoxybutane, 1,2-epoxycyclohexane, epichlorohydrin, styrene oxides, p-chlorostyrene oxide, and mixtures of two or more of these. Ethylene oxide, propylene oxide, or mixtures thereof are particularly preferred for post-treatment of the reaction mixture.

This post-treatment involves contacting the reaction mixture with the epoxide or mixture of epoxides at a reaction temperature from about 25° C. up to the decomposition temperature of the reaction mixture. A stoichiometric excess of the epoxide relative to the residual acidity of the reaction mixture is normally used in this post-treatment. The amount of the excess is not critical and will usually range from about a 0.1 mole excess up to about a ten mole excess. This post-treatment may be carried out at atmospheric, subatmospheric, or superatmospheric pressure and can be conducted in the presence or absence of added solvents or diluents as reaction media. Suitable solvents and diluents are mentioned hereinbefore. Excess epoxide can function as the reaction medium if desired.

Several series or different phosphinothioylthio compounds are useful in preparing the compounds of this invention. These useful reactants are of the following types:

1. Dihydrocarbylphosphinodithioic acids (in which a and b are each zero), such as diethylphosphinodithioic acid, corresponding to the formula, $(C_2H_5)_2P(S)SH$;

2. S-hydrocarbyl hydrogen hydrocarbylphosphonotrithioates (in which a is 1, b is zero, and $X^4$ is sulfur), such as S-ethyl hydrogen ethylphosphonotrithioate, corresponding to the formula $(C_2H_5)(C_2H_5S)P(S)SH$;

3. O-hydrocarbyl hydrogen hydrocarbylphosphonodithioates (in which a is 1, b is zero, and $X^1$ is oxygen), such as O-ethyl hydrogen ethylphosphonodithioate, corresponding to the formula $(C_2H_5)(C_2H_5O)P(S)SH$;

4. Dihydrocarbyl hydrogen phosphorotetrathioates (in which a and b are each 1 and $X^1$ and $X^2$ are sulfur), such as diethyl hydrogen phosphorotetrathioate, corresponding to the formula $(C_2H_5S)_2P(S)SH$;

5. O,S-dihydrocarbyl hydrogen phosphorotrithioates (in which a and b are each 1, $X^1$ is oxygen and $X^2$ is sulfur), such as O,S-diethyl hydrogen phosphorotrithioate, corresponding to the formula $(C_2H_5O)(C_2H_5S)P(S)SH$; and 6. O,O-dihydrocarbyl hydrogen phosphorodithioates (in which a and b are each 1 and $X^1$ and $X^2$ are oxygens), such as O,O-diethyl hydrogen phosphorodithioate, corresponding to the formula $(C_2H_5O)_2P(S)SH$. Such compounds are preferred.

The terminology "hydrocarbon-based" or "hydrocarbon-based radical" as used herein and in the appended claims is used to define a monovalent radical which is derived from a hydrocarbon by removal of a hydrogen from a carbon atom of the hydrocarbon, said carbon atom being directly attached to the remainder of the molecule. These hydrocarbon-based radicals may be derived from aliphatic, cycloaliphatic, aromatic, mixed aliphatic-cycloaliphatic, mixed aliphatic-aromatic, or mixed cycloaliphatic-aromatic hydrocarbons. As is discussed more fully below, the hydrocarbons from which these radicals are derived may contain certain substituents. Thus, "hydrocarbon-based" is a generic expression for (1) hydrocarbon and (2) substituted hydrocarbon radicals.

The hydrocarbon-based radicals in the compounds of this invention are substantially saturated. The terminology "substantially saturated" as used herein is intended to define radicals free from acetylenic unsaturation (—C≡C—) in which there is not more than one (1) ethylenic linkage (>C=C<) for every eight (8) carbon-to-carbon covalent bonds. The so-called "double bonds" in aromatic rings (e.g., benzene) are not to be considered as contributing to unsaturation with respect to the terminology "substantially saturated". Usually there will be no more than an average of one (1) ethylenic linkage per substantially saturated monovalent radical as described hereinbefore. Preferably (with the exception of aromatic rings), all the carbon-to-carbon bonds in a substantially saturated radical will be saturated linkages; that is, the radical will be free from acetylenic and ethylenic linkages.

In general, the hydrocarbon-based radicals may contain up to about thirty (30) carbon atoms with a preferred range of carbon atoms being from one (1) up to about twenty (20). The subject radicals may contain certain nonreactive non-hydrocarbon substituents. As a general rule, and particularly, when the compounds of this invention are to be used as lubricant additives, the degree of substitution and nature of the substituent on the hydrocarbon-based radicals is such that the essentially hydrocarbon character of the radical is not destroyed. Thus, in view of this requirement, these radicals normally, have no more than four (4) substituents per radical, and usually, not more than one (1) substituent for every ten (10) carbon atoms in the radical.

As used herein and in the appended claims, the terminology "hydrocarbyl" is used to define those radicals containing no non-hydrocarbon substituent and the terminology "substituted hydrocarbyl" is used to define those radicals derived from the above described hydrocarbon radicals but containing a non-hydrocarbon substituent. Thus, the following are representative examples of hydrocarbon radicals: (1) alkyl, such as ethyl, t-butyl, isooctyl, dodecyl and eicosyl; (2) alkenyl, such as allyl, 2-pentenyl and dodecenyl; (3) cycloalkyl, such as cyclooctyl and cyclobutyl; (4) cycloalkenyl, such as cyclopentenyl and cycloheptenyl; (5) aryl, such as phenyl, naphthyl, and diphenyl; (6) cycloalkylalkyl, such as cyclopropylethyl and cyclooctylbutyl; (7) cycloalkenylalkyl, such as cyclohexenylpropyl and cyclopentenylmethyl; (8) arylalkyl, such as benzyl, phenylethyl, tolyldecyl and naphthylethyl; (9) arylalkenyl, such as phenylvinylene and 2-xylylallyl; (10) alkylcycloalkyl, such as trimethylcyclododecyl and butylcycloheptyl; (11) alkenylcycloalkyl, such as vinylcyclopentyl and butylenecyclooctyl; (12) alkylcycloalkenyl, such as butylcyclohexenyl and methylcyclooctenyl; (13) alkenylcycloalkenyl, such as vinylcyclopentenyl and butylenecycloheptenyl; (14) arylcycloalkyl, such as xylylcyclodecyl and naphthylcyclohexyl; (15) arylcycloalkenyl, such as phenylcyclohexenyl and tolylcyclododecenyl; (16) alkylaryl, such as tolyl, xylyl, dodecylphenyl and didodecylphenyl; (17) alkenylaryl, such as allylphenyl, octenylphenyl and 2-butenylphenyl; (18) cycloalkylaryl, such as cyclobutylphenyl and cyclohexylnaphthyl; (19) cycloalkenylaryl, such as cyclopentenylphenyl and cyclohexenylphenyl.

The preferred hydrocarbon radicals are alkyl, phenyl, naphthyl, alkylphenyl, alkylnaphthyl, phenylalkyl, naphthylalkyl, alkylphenylalkyl, and alkylnaphthylalkyl. Alkyl, phenyl, alkylphenyl, phenylalkyl, and alkylphenylalkyl are most preferred.

Representative non-hydrocarbon substituents for the substituted hydrocarbon radicals include halo substituents, such as chloro, fluoro, bromo, and iodo; nitro; lower alkoxy, such as butoxy and hexyloxy; lower alkylthio, such as pentylthio and heptylthio; hydroxy; and mercapto. The terminology "lower" describes radicals having groups of up to seven (7) carbon atoms.

A clear understanding of the compounds of this invention, processes for their preparation, and lubricant compositions containing them may be obtained from the examples given below, which illustrate the presently preferred best modes for carrying out the invention.

EXAMPLE 1

A solution of 40.4 grams (0.4 mole) of N-hydroxymethylacrylamide, 50 grams of ethanol and 5 grams of water is prepared in a suitable reactor. This solution is cooled to about 20° C., and 244 grams (0.8 mole) of a O,O-dialkylhydrogen phosphorodithioate is added over a period of about 1 hour, with the reaction temperature in the range of 20°-28° C. The specific phosphorodithioate used is a mixed ester being approximately 65% of the isobutyl ester and approximately 35% of the n-amyl ester. The reaction mixture is stirred at room temperature for 5 hours and then allowed to stand for an additional period of about 16 hours. After stirring at 40° C. for about two (2) hours, the acidity of the reaction mixture is lowered by treatment with an additional 2.5 grams of N-hydroxymethylacrylamide and stirring for about two (2) hours at 40°-60° C., followed by an additional treatment with 2.0 grams of the amide. The reaction mixture is then stripped at 75° C. under reduced pressure, 50 grams of benzene is added, and this mixture is stripped at 100° C. under reduced pressure. A yield of 265 grams of crude material is obtained. This crude material is filtered to yield, as the filtrate, 249 grams (86% yield) of purified, N-(dialkoxyphosphinothioylthiomethyl) 3-(dialkoxyphosphinothioylthio) propionamide, wherein the alkoxy groups are about 65% isobutyloxy and about 35% n-amyloxy groups.

EXAMPLE 2

O,O-diisooctyl hydrogen phosphorodithioate (107 grams, 0.25 mole) is charged to a reactor and stirred for one (1) hour at room temperature while nitrogen is blown through at a rate of 1 cubic foot per hour (cfh). N-hydroxymethylacrylamide (25 grams, 0.25 mole) is rapidly added to the reactor, and the resulting mixture is stirred for eight (8) hours at room temperature with nitrogen being blown over the mixture at the rate of 0.5 cfh. Benzene (50 grams) is then added to the reaction mixture and the resulting mixture stirred for an additional six (6) hour period at room temperature. At the end of this period, the mixture is filtered to remove the white solid material and the filtrate stripped under reduced pressure at 57° C. The stripped filtrate is filtered to yield 114 grams (93% yield) of a green liquid product, N-(diisooctyloxyphosphinothioylthiomethyl) 3-(diisooctyloxyphosphinothioylthio)propionamide.

EXAMPLE 2A

Repeating the above general procedure, 429 grams (1.0 mole) of an O,O-dialkyl hydrogen phosphorodithioate is charged to a reactor and stirred at room temperature for about one hour, while nitrogen gas is blown through at a rate of about 0.25 cfh. The specific phosphorodithioate used is a mixed ester being approximately 30% of the decyl ester and approximately 70% of the isooctyl ester. After cooling to about 18° C., 101 grams (1.0 mole; 100% excess) of N-hydroxymethylacrylamide is added and the resulting mixture is allowed to react for approximately eight (8) hours at room temperature. During the initial reaction period some external cooling of this mixture is desirable due to exotherming of the mixture. At the end of this reaction period, 200 grams of benzene is added and the resulting mixture stirred for about six (6) hours at room temperature. The excess solid N-hydroxymethylacrylamide is filtered off, and after washing with an aliphatic petroleum naphtha and drying, a 50-51 gram portion of solid material (excess N-hydroxymethylacrylamide) will be obtained. The filtered solution is stripped under reduced pressure at about 67° C. to yield crude material, which upon filtration yields 408 grams (86% yield) of purified N-(dialkoxyphosphinothioylthiomethyl) 3-(dialkoxyphosphinothioylthio)propionamide, wherein the alkoxy groups are about 30% decyloxy and about 70% isooctyloxy groups.

A portion (303 grams, 0.035 mole) of the above product is charged to a reactor and treated at room temperature with 8.3 grams (0.14 mole) of propylene oxide. The propylene oxide treatment is effective by the addition of 2.3 grams of propylene oxide followed by stirring the resulting mixture for about four (4) hours, the addition of 4 grams of propylene oxide followed by three (3) hours of stirring, and the addition of 2 grams of propylene oxide followed by three (3) hours of stirring. Upon completion of the treatment with propylene oxide, the reaction mixture is stripped under reduced pressure at 40° C. and then filtered. The filtrate yields 271 grams (89% yield) of the reaction product.

EXAMPLE 3

Following the general procedure of Example 1, the O,O-dialkyl hydrogen phosphorodithioate is replaced with 0.8 mole of diphenylphosphinodithioic acid, or S-benzyl hydrogen benzylphosphonotrithioate, or O-decylphenyl hydrogen decylphenylphosphonodithioate, or diethoxypropyl hydrogen phosphorotetrathioate, or O,S-dipentadecyl hydrogen phosphorotrithioate, and yields of the corresponding, N-(diphenylphosphinothioylthiomethyl) 3-(diphenylphosphinothioylthio)propionamide; or N-(benzylbenzylthiophosphinothioylthiomethyl) 3-(benzylbenzylthiophosphinothioylthio)propionamide; or N-(decylphenyloxydecylphenylthiophosphinothioylthiomethyl) 3-decylphenyloxydecylphenylthiophosphinothioylthio)propionamide; of N-(diethoxypropylthiophosphinothioylthiomethyl) 3-(diethoxypropylthiophosphinothioylthio)propionamide; or N-(pentadecyloxypentadecylthiophosphinothioylthiomethyl) 3-pentadecyloxypentadecylthiophosphinothioylthio)-propionamide; are obtained.

EXAMPLE 4

Following the general procedure of Example 1, 0.4 mole of N-hydroxymethylthioacrylamide is reacted with 0.8 mole of: O,O-dicyclohexyl hydrogen phosphorodithioate, or O,S-ditolyl hydrogen phosphorotrithioate, or dibenzyl hydrogen phosphorotetrathioate, or O-2-ethylhexyl hydrogen 2-ethylhexylphosphonodithioate, or S-naphthyl hydrogen naphthylphosphonotrithioate, or dihexylphosphinodithioic acid, to give the corresponding, N-(dicyclohexyloxyphosphinothioylthiomethyl) 3-(dicyclohexyloxyphosphinothioylthio)thiopropionamide, or N-(tolyloxytolylthiophosphinothioyl-thiomethyl) 3-(tolyloxytolylthiophosphinothioylthio)-thiopropionamide, or N-(dibenzylthiophosphinothioyl-thiomethyl) 3-(dibenzylthiophosphinothioylthio)thio-propionamide, or N-(2'-ethylhexyloxy-2'-ethylhexyl-phosphinothioylthiomethyl) 3-(2'-ethylhexyloxy-2'-ethylhexylphosphinothioylthio)thiopropionamide, or N-(naphthylnaphthylthiophosphinothioylthiomethyl) 3-(naphthylnaphthylthiophosphinothioylthio)-thiopro-pionamide, or N-(dihexylphosphinothioylmethyl) 3-dihexylphosphinothioylthio)thiopropionamide.

EXAMPLE 5

Following the general procedure in Example 1, 0.4 mole N-hydroxymethylmethacrylamide is reacted with 0.08 mole of diphenylphosphinodithioic acid, to yield N-(diphenylphosphinothioylthiomethyl) 3-(diphenyl-phosphinothioylthio)-2-methylpropionamide.

EXAMPLE 6

Following the general procedure in Example 1, 0.4 mole of N-hydroxymethyl-2-chloroacrylamide is reacted with 0.8 mole of S-benzyl hydrogen benzylphos-phonotrithioate, to yield N-(benzylbenzylthiophos-phinothioylthiomethyl) 3-(benzylbenzylthiophosphino-thioylthiomethyl)-2-chloropropionamide.

EXAMPLE 7

Following the general procedure of Example 1, 0.4 mole of 2-heptylacrylamide is reacted with 0.8 mole of O-decylphenyl hydrogen decylphenylphosphonodithi-oate, to yield N-(decylphenyloxydecylphenylphos-phinothioylthiomethyl) 2-(decylphenyloxydecyl-phenylphosphinothioylthiomethyl)nonanamide.

EXAMPLE 8

Following the general procedure of Example 1, 0.4 mole of N-hydroxymethyl-2-(3'-propoxypropyl)acryla-mide is reacted with 0.8 mole of O,O-diisooctyl hydrogen phosphorodithioate to yield, N-(diisooctyloxyphos-phinothioylthiomethyl) 2-(diisooctylphosphinothioyl-thiomethyl)-5-propoxyvaleramide.

EXAMPLE 9

Following the procedure of Example 1, 0.4 mole of N-hydroxymethyl-2-isobutylacrylamide is reacted with 0.8 mole of diethoxypropyl hydrogen phosphorotetra-thioate to yield N-(diethoxypropylthiophosphinothioyl-thiomethyl) 2-(diethoxypropylthiophosphinothioylthi-omethyl)-4-methylvaleramide.

EXAMPLE 10

Following the general procedure used in Example 1, 0.4 mole of N-hydroxymethyl-2-bromoacrylamide is reacted with 0.8 mole of O,S-dipentadecyl hydrogen phosphorotrithioate to yield N-(pentadecyloxypen-tadecylthiophosphinothioylthiomethyl) 2-bromo-3-(pentadecyloxypentadecylthiophosphinothioylthio)-propionamide.

EXAMPLE 11

Following the general procedure of Example 1, 0.4 mole of N-hydroxymethyl 2-(5'-chloropentyl)acryla-mide is reacted with 0.8 mole of O,O-dicyclohexyl hydrogen phosphorodithioate, to yield N-(dicyclohex-yloxyphosphinothioylthiomethyl) 7-chloro-2-(dicy-clohexyloxyphosphinothioylthiomethyl)heptamide.

EXAMPLE 12

Following the general procedure of Example 1, 0.4 mole of N-hydroxymethyl 2-hexylthioacrylamide is reacted with 0.8 mole of O,S-ditolyl hydrogen phos-phorotrithioate, to yield N-(tolyloxytolylthiophos-phinothioylthiomethyl) 2-(tolyloxytolylthiophosphino-thioylthiomethyl)thiooctanamide.

EXAMPLE 13

Following the general procedure of Example 1, 0.4 mole of N-hydroxymethylthiomethacrylamide is reacted with 0.8 mole of dibenzyl hydrogen phos-phorotetrathioate, to yield N-(dibenzylthiophosphino-thioylthiomethyl) 3-(dibenzylthiophosphinothioylthio)-2-methylthiopropionamide.

EXAMPLE 14

Following the general procedure of Example 1, 0.4 mole of N-hydroxymethyl 2-chlorothioacrylamide is reacted with 0.8 mole of O-2-ethylhexyl hydrogen 2-ethylhexylphosphonodithioate, to yield N-(2'-ethylhex-yloxy-2'-ethylhexylphosphonothioylthiomethyl) 2-chloro-3-(2'-ethylhexyloxy-2'-ethylhexylphosphonothi-oylthio)thiopropionamide.

As was briefly discussed above, the compounds of this invention are particularly useful as additives for lubricating oils in the formulation of lubricating compositions. It is well known in the art that when lubricating oils are subjected to extended periods of use, particularly at high operating temperatures, they tend to decompose with the formation of various oxidation products, such as acidic materials, peroxides and other decomposition products. These products have many adverse effects upon both the base lubricating oil and upon the various materials which come into contact with the lubricating composition. Thus, these products promote the corrosion of various metallic surfaces, such as engine parts, gears, etc., contacted with compositions containing the various oxidation and other decomposition products. Corrosion of these metallic surfaces promotes among other adverse effects, excessive wear of the surfaces. It is common practice to incorporate in a lubricating oil compounds capable of increasing the resistance of these oils to oxidation, i.e., oxidation inhibitors, as well as improving many other properties of the base lubricating oil by the addition of other additives for various other functions. Thus, the compounds of this invention are particularly useful as additives for lubricating oils where they function primarily as oxidation inhibitors, corrosion inhibitors, antiwear agents and extreme pressure agents.

Lubricating compositions containing the compounds of this invention as additives comprise a major proportion of a lubricating oil and a minor proportion, sufficient to improve the oxidation stability or the oxidation inhibiting properties of the composition, of at least one of said compounds. In general, the compounds are used in lubricants in amounts of about 0.01–20.0% by weight. The optimum concentration for a particular additive will depend to a large measure upon the type of service to which the composition is to be subjected. In most applications, lubricating compositions containing about 0.1–10.0% by weight are useful, although for certain applications, such as in gear lubricants and diesel engines, compositions containing up to 20% or more may be preferred.

The compounds of this invention can be effectively employed in a variety of lubricating compositions formulated for a variety of uses. Thus, lubricating compositions containing the subject additive are effective as crankcase lubricating oils for spark-ignited and compression-ignited internal combustion engines, including automobile and truck engines, two-cycle engines, aviation piston engines, marine and low-load diesel engines, and the like. Also, automatic transmission fluids, transaxle lubricants, gear lubricants, metal-working lubricants, hydraulic fluids, and other lubricating oil and grease compositions can benefit from the incorporation of the compounds of this invention.

The lubricating compositions of the present invention may, of course, be prepared by a variety of methods known in the art. One convenient method is to add the aforementioned compound in the form of a concentrated solution or substantially stable suspension to a sufficient amount of the base lubricant to form the subject lubricating compositions. This additive concentrate contains the compound in the proper amount to provide the proper ratio of additive in the final lubricating composition when added to a predetermined amount of base lubricant. The concentrate may also contain appropriate amounts of other additives which it is desired to incorporate in the final lubricating composition.

Generally, the concentrate will comprise about 20–90% by weight of the compound of this invention with the balance being a substantially inert normally liquid solvent or diluent, plus any other additives used. Suitable solvents and diluents include any of the herein discussed natural or synthetic oils, kerosene, xylene, benzene, mixtures of two or more of these and other solvents and diluents known in the art. Hereinafter, these substantially inert, normally liquid solvents and diluents used in the preparation of additive concentrates are referred to collectively as carriers. Normally the carriers are oil-soluble at least to the extent of their concentration in the final lubricating compositions prepared from them.

The compounds of this invention are effectively employed using base oils of lubricating viscosity derived from a variety of sources. Thus, base oil derived from both natural and synthetic sources are useful for the preparation of lubricating compositions.

The natural oils include animal oils, such as lard oil; vegetable oils, such as castor oil; and mineral oils, such as solvent-treated or acid-treated mineral oils of the paraffinic, naphthenic, or mixed paraffinic-naphthenic types. Also useful are oils of lubricating viscosity derived from coal or shale.

Many synthetic lubricants are known in the art and these are useful as base lubricating oils. Surveys of synthetic lubricants are contained in the publications, SYNTHETIC LUBRICANTS by R. C. Gunderson and A. W. Hart, published by Reinhold (N.Y., 1962) and LUBRICATION AND LUBRICANTS, E. R. Braithwaite, ed., published by Elseiver Publishing Co., (N.Y., 1967), Chapter 4, pages 166 through 196, "Synthetic Lubricants". These publications are incorporated herein by reference to establish the state of the art in regard to identifying both general and specific types of synthetic lubricants which can be used in conjunction with the compounds of this invention.

Thus, useful synthetic lubricating base oils include hydrocarbon oils derived from the polymerization or copolymerization of olefins, such as polypropylene, polyisobutylene and propylene-isobutylene copolymers; and the halo-hydrocarbon oils, such as chlorinated polybutylene. Other useful synthetic base oils include those based upon alkyl benzenes, such as dodecylbenzene, tetradecylbenzene, and those based upon polyphenols, such as biphenyls, and terphenyls.

Another known class of synthetic oils useful as base oils are those based upon alkylene oxide polymers and interpolymers, and those oils obtained by the modification of the terminal hydroxy groups of these polymers, (i.e., by the esterification or etherification of the hydroxy groups). Thus, useful base oils are obtained from polymerized ethylene oxide or propylene oxide or from the copolymers of ethylene oxide and propylene oxide. Useful oils include the alkyl and aryl ethers of the polymerized alkylene oxides, such as methylpolyisopropylene glycol ether, diphenyl ether of polyethylene glycol, and diethyl ether of propylene glycol. Another useful series of synthetic base oils is derived from the esterification of the terminal hydroxy group of the polymerized alkylene oxides with mono- or polycarboxylic acids. Exemplary of this series is the acetic acid esters or mixed $C_3$–$C_8$ fatty acid esters of the $C_{13}$ Oxo acid diester of tetraethylene glycol.

Another suitable class of synthetic lubricating oil comprises the esters of dicarboxylic acids, such as phthalic acid, succinic acid, oleic acid, azelaic acid, suberic acid, sebacic acid, with a variety of alcohols. Specific examples of these esters include dibutyl adipate, di(2-ethylhexyl)sebacate, and the like. Silicone based oils such as polyalkyl-, polyaryl-, polyalkoxy-, or polyaryloxy-siloxane oils and the silicate oils, i.e., tetraethyl silicate, comprise another useful class of synthetic lubricants. Other synthetic lubricating oils include liquid esters of phosphorus-containing acid, such as tricresyl phosphate, polymerized tetrahydrofurans, and the like.

Unrefined, refined, and re-refined oils of the type described above are useful as base oil for the preparation of lubricant compositions of this invention. Unrefined oils are those obtained directly from a natural or synthetic source without further purification or treatment. For example, a shale oil obtained directly from retorting operations, a petroleum oil obtained directly from distillation, or an ester oil obtained directly from an esterification process, and used without further treatment are unrefined oils. Refined oils are similar to the unrefined oils, except they have been further treated in one or more purification steps, to improve one or more properties. Many such purification techniques are known in the art, such as solvent extraction, acid or base extraction, filtration, percolation, etc. Rerefined oils are obtained by a variety of processes similar to those used to obtain refined oils. The rerefined oils are also known as reclaimed or reprocessed oils and have been treated by additional techniques directed to the removal of spent additives and oil breakdown products.

The compounds of this invention can be used alone or in combination with other lubricant additives known in the prior art. Brief surveys of conventional additives for lubricating compositions are contained in the publications, LUBRICANT ADDITIVES, by C. V. Smalheer and R. Kennedy Smith, published by the Lezius-Hiles Co., Cleveland, Ohio (1967) and LUBRICANT ADDITIVES, by M. W. Ranney, published by Noytes Data Corp., Park Ridge, New Jersey (1973). These publications are incorporated herein by reference to establish the state of the art in regard to identifying both general and specific types of other additives which can be used in conjunction with the compounds of this invention.

In general, these additional additives include detergents of the ash-containing type, ashless dispersants, viscosity index improvers, pour point depressants, anti-foam agents, extreme pressure agents, anti-wear agents, rust-inhibiting agents, oxidation inhibitors, and corrosion inhibitors.

The ash-containing detergents are the well known neutral basic alkali or alkaline earth metal salts of sulfonic acids, carboxylic acids or organo-phosphorus-containing acids. The most commonly used salts of these acids are the sodium, potassium, lithium, calcium, magnesium, strontium, and barium salts. The calcium and barium salts are used more extensively than the others. The "basic salts" are those metal salts known to the art wherein the metal is present in a stoichiometrically larger amount than that necessary to neutralize the acid. The calcium- and barium-overbased petrosulfonic acids are typical examples of such basic salts.

The extreme pressure agents, corrosion-inhibiting agents, and oxidation-inhibiting agents, are exemplified by chlorinated aliphatic hydrocarbons, such as chlorinated wax; organic sulfides and polysulfides, such as benzyl-disulfide, bis-(chlorobenzyl)disulfide, dibutyl tetrasulfide, sulfurized sperm oil, sulfurized methyl ester of oleic acid, sulfurized alkylphenol, sulfurized dipentene, sulfurized terpene, and sulfurized Diels-Alder adducts; phosphosulfurized hydrocarbons, such as the reaction product of phosphorus sulfide with turpentine or methyloleate; phosphorus esters such as the dihydrocarbon and trihydrocarbon phosphites, i.e., dibutyl phosphite, diheptyl phosphite, dicyclohexyl phosphite, pentylphenyl phosphite, dipentylphenyl phosphite, tridecyl phosphite, distearyl phosphite, and polypropylene substituted phenol phosphite; metal thiocarbamates, such as zinc dioctyldithiocarbamate and barium heptylphenol dithiocarbamate; and Group II metal salts of phosphorodithioic acid, such as zinc dicyclohexyl phosphorodithioate, and the zinc salts of a phosphorodithioic acid.

The ashless detergents or dispersants are a well known class of lubricant additives and are extensively discussed and exemplified in the above-cited publications by Smalheer et al. and Ranney and the references cited therein. Particularly useful types of ashless dispersants are based upon the reaction products of hydrocarbon-substituted succinic acid compounds and polyamines or polyhydric alcohols. These reaction products may be post-treated with materials, such as alkylene oxides, carboxylic acids, boron compounds, carbon disulfide and alkenyl cyanides to produce further useful ashless dispersants.

Pour point depressing agents are illustrated by the polymers of ethylene, propylene, isobutylene, and poly-(alkyl methacrylate). Anti-foam agents include polymeric alkyl siloxanes, poly(alkyl methacrylates), terpolymers of diacetone acrylamide and alkyl acrylates or methacrylates, and the condensation products of alkyl phenols with formaldehyde and an amine. Viscosity index improvers include polymerized and copolymerized alkyl methacrylates and polyisobutylenes.

When additional additives are used in lubricant compositions comprising the compounds of this invention, they are used in concentrations in which they are normally employed in the art. Thus, they will generally be used in a concentration of about 0.001–25.0% by weight of total composition, depending, of course, upon the nature of the additive and the nature of the lubricant composition. For example, ashless dispersants can be employed in amounts of about 0.1–10.0% and metal-containing detergents in amounts of about 0.1–20.0% by weight. Other additives, such as pour point depressants, extreme pressure additives, viscosity index improving agents, antifoaming agents, and the like, are normally employed in amounts of about 0.001–10.0%, depending upon the nature and purpose of the particular additive.

The following compositions exemplify the incorporation of the compounds of this invention into lubricants.

EXAMPLE A

A lubricating composition suitable for use as a crankcase lubricant is prepared using as the base oil, an equal volume mixture of a 100 N mineral lubricating oil and a 200 N mineral lubricating oil and, as additives: 8.69% of a polyisodecylacrylate viscosity index improver; 5.84% of a dispersant which is a reaction product of a polyisobutenylsuccinic anhydride and pentaerythritol in a 1:1 equivalent ratio; 1.58% of a dispersant based upon the reaction product of an acylating agent (prepared from chlorinated polyisobutene and acrylic acid) with tetraethylene pentamine and phthalic acid; 1.32% of an oxidation inhibitor and wear agent based upon a sulfurized Diels-Alder adduct of a conjugated diene and an alkyl acrylate; 0.83% of the product of Example 1; and 0.25% of a commercial thiadiazole based copper deactivator commercially available as Amoco 150.

In the above lubricating composition, the subject compound is used as an additive, principally, for its antioxidant and antiwear properties.

EXAMPLE B

A lubricating composition suitable for use as an automatic transmission fluid is prepared using as the base oil, a mixture of 90% by volume of a 110 N mineral lubricating oil and 10% by volume of a 210 N mineral lubricating oil, and as additives: 4.0% of the reaction product of polyisobutenyl succinic anhydride, tetraethylene pentamine, and carbon disulfide as disclosed in U.S. Pat. No. 3,251,185, as a dispersant and oxidation inhibitor; 1% of a corrosion inhibitor which is the reaction product of a polyisobutenyl succinic anhydride, tetraethylene pentamine, and boric acid as described in U.S. Pat. No. 3,254,025; 0.71% of the product of Example 1; and 0.2% of a conventional friction modifier, based upon Polyoxyethylene (2) Tallowamine (Ethomeen T/12).

In the above lubricating composition, the subject compound is used as an additive, principally, for its antioxidant and antiwear properties.

EXAMPLE C

A lubricating composition suitable for use as a gear lubricant is prepared using a SAE 90 base mineral oil, and as additives: 2.29% of an antiwear agent based upon a sulfurized methyl ester of tall oil acid having a sulfur content of 15%; 1.26% of an EP agent based upon sulfurized isobutylene; 0.17% of a rust inhibitor based upon a fatty acid derivative of oxazoline; 0.2% of the product of Example 1; and 0.1% of tri(4-methyl-2-pentyl)phosphite as an extreme pressure agent.

In the above lubricating composition, the subject compound is used as an additive, principally, for its antioxidant and extreme pressure properties.

EXAMPLE D

A lubricating composition is prepared using a synthetic lubricating base oil consisting essentially of the diethyl ether of propylene glycol having an average molecular weight of about 1500, and 1% of the product of Example 1.

EXAMPLE E

A lubricating composition suitable for use as a turbine lubricating oil is prepared using a 200 N mineral base oil and as additives: 0.05% of an oil solution (37% oil) of a partially esterified, approximately 5%, reaction product of dodecenyl succinic acid and propylene oxide, as a rust inhibitor; and 1.39% (0.1% P) of the product of Example 1.

In the above lubricating composition, the subject compound is used as an additive, principally, for its antioxidant properties.

EXAMPLE F

A lubricating composition suitable for use as a crankcase lubricant is prepared using as the base oil, a mixture of 60% by volume (60.35% by weight) of a 200 N mineral lubricating oil and 40% by volume (39.65% by weight) of a 100 N mineral lubricating oil, and as additives: 8.7% of the viscosity index improver of Example A; 5.85% of the ester dispersant of Example A; 1.58% of the acylated nitrogen dispersant of Example A; 1.32% of the oxidation inhibitor and wear agent of Example A; 0.25% of the copper deactivator of Example A; 40 ppm of a silicone-based anti-foam agent; and 0.85% of the product of Example 2A.

In the above lubricating composition, the subject compound is used as an additive, principally, for its antioxidant and antiwear properties.

What is claimed is:

1. A method of preparing a compound having the formula:

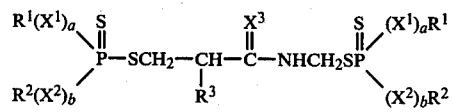

which comprises reacting at a temperature of about 0° to 100° C. an amide or thioamide compound of the formula

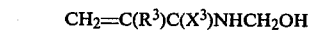

with a phosphorus-containing compound of the formula:

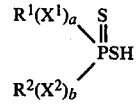

wherein each of $R^1$ and $R^2$ is a hydrocarbon-based radical; $R^3$ is a hydrogen, halogen, lower alkyl or substituted lower alkyl radical; each of $X^1$, $X^2$, and $X^3$ is oxygen or sulfur; and a and b are each 0 or 1; and at least about two moles of the phosphorus compound are used per one mole of the amide or thioamide.

2. A method according to claim 1 wherein $X^3$ is oxygen.

3. A method according to claim 2 wherein $R^1$ and $R^2$ are hydrocarbon radicals, $X^1$ and $X^2$ are oxygen and a and b are each 1.

4. A method according to claim 3 wherein $R^3$ is hydrogen.

5. A method according to claim 3 wherein $R^3$ is lower alkyl.

6. A method according to claim 1 wherein each of $R^1$ and $R^2$ is a hydrocarbon radical selected from t-butyl, isobutyl, amyl, isooctyl, decyl, dodecyl, eicosyl, 2-pentenyl, dodecenyl, phenyl, naphthyl, alkylphenyl, alkylnaphthyl, phenylalkyl, naphthylalkyl, alkylphenylalkyl, and alkylnaphthylalkyl, $R^3$ is hydrogen, $X^1$, $X^2$ and $X^3$ are oxygen, and a and b are each 1.

7. A method as claimed in claims 1,2,3,4,5 or 6 wherein said amide or thioamide is present in excess of the stoichiometric amount.

8. A method as claimed in claims 1,2,3,4,5 or 6 wherein the reaction is carried out at a temperature of about 25°–80° C.

9. A method as claimed in claim 1 wherein the reaction is carried out at a temperature of about 25°–80° C. and said amide or thioamide is present in excess of the stoichiometric amount.

* * * * *